(12) United States Patent
Specht et al.

(10) Patent No.: US 11,471,131 B2
(45) Date of Patent: Oct. 18, 2022

(54) ULTRASOUND IMAGING SYSTEM AND METHOD FOR DISPLAYING AN ACQUISITION QUALITY LEVEL

(71) Applicant: General Electric Company, Schenectady, NY (US)

(72) Inventors: Tanya Specht, Hempstead, NY (US); Menachem Halmann, Milwaukee, WI (US); Alexander Sokulin, Kiryat (IL); Peter Lysyansky, Haifa (IL); Cynthia Owen, Powhatan, AR (US); Sergey Ogurtsov, Haifa (IL)

(73) Assignee: General Electric Company, Schenectady, NY (US)

( * ) Notice: Subject to any disclaimer, the term of this patent is extended or adjusted under 35 U.S.C. 154(b) by 243 days.

(21) Appl. No.: 16/936,941

(22) Filed: Jul. 23, 2020

(65) Prior Publication Data

US 2020/0352548 A1    Nov. 12, 2020

Related U.S. Application Data

(63) Continuation of application No. 15/581,004, filed on Apr. 28, 2017, now Pat. No. 10,799,219.

(51) Int. Cl.
*A61B 8/08* (2006.01)
*A61B 8/00* (2006.01)
*G06T 7/00* (2017.01)
*G09B 23/28* (2006.01)

(52) U.S. Cl.
CPC ............ *A61B 8/5269* (2013.01); *A61B 8/463* (2013.01); *A61B 8/469* (2013.01); *A61B 8/5207* (2013.01); *G06T 7/0012* (2013.01); *G09B 23/286* (2013.01); *A61B 8/54* (2013.01)

(58) Field of Classification Search
CPC ....... G09B 23/286; A61B 8/5269; A61B 8/46; A61B 8/461; A61B 8/463; A61B 8/465; A61B 8/468; A61B 8/469; A61B 8/52; A61B 8/54; G06T 7/0012; G06T 7/0014
See application file for complete search history.

(56) References Cited

U.S. PATENT DOCUMENTS

| | | | |
|---|---|---|---|
| 6,670,963 B2 | 12/2003 | Osberger | |
| 7,424,147 B2 | 9/2008 | Obrador | |
| 9,072,493 B1 | 7/2015 | Yoshikawa | |
| 9,489,921 B2 | 11/2016 | Nam | |
| 2012/0226160 A1* | 9/2012 | Kudoh | A61B 8/461 600/443 |
| 2013/0002264 A1* | 1/2013 | Garber | A61B 5/08 324/600 |

(Continued)

OTHER PUBLICATIONS

Cikes, Maja, et al. "Ultrafastcardiac ultrasound imaging: technical principles, applications, and clinical benefits." JACC: Cardiovascular Imaging 7.8 (2014): 812-823.*

(Continued)

*Primary Examiner* — Carolyn A Pehlke

(57) ABSTRACT

A system and a method of ultrasound imaging includes acquiring ultrasound data, acquiring a quality parameter while acquiring the ultrasound data, determining an acquisition quality level based on the quality parameter, displaying an image generated based on the ultrasound data and displaying an ROI on the ultrasound image, where a color of the ROI represents the acquisition quality level.

20 Claims, 9 Drawing Sheets

(56) References Cited

U.S. PATENT DOCUMENTS

2013/0190600 A1\* 7/2013 Gupta ............... A61B 8/0866
  600/407
2018/0161010 A1\* 6/2018 Choi .................. A61B 8/54
2019/0125298 A1\* 5/2019 Abolmaesumi ...... A61B 8/4405

OTHER PUBLICATIONS

CN application 201810396920.8 filed Apr. 27, 2018—2nd Office Action dated Feb. 26, 2021; 8 pages.

\* cited by examiner

ULTRASOUND IMAGING SYSTEM AND METHOD FOR DISPLAYING AN ACQUISITION QUALITY LEVEL

RELATED APPLICATIONS

This patent arises from a continuation of U.S. patent application Ser. No. 15/581,004, entitled "ULTRASOUND IMAGING SYSTEM AND METHOD FOR DISPLAYING AN ACQUISITION QUALITY LEVEL", filed Apr. 28, 2017, which is incorporated herein by reference in its entirety.

FIELD OF THE INVENTION

This disclosure relates generally to an ultrasound imaging system and method for displaying a border on an image to indicate an ROI, where the color of the border represents an acquisition quality level.

BACKGROUND OF THE INVENTION

Ultrasound imaging procedures are oftentimes used to acquire quantitative or qualitative information from a region-of-interest (ROI). An ultrasound imaging system may automatically calculate a patient parameter such as a length or diameter of an anatomical structure, a volume of blood or fluid flowing through a region in a period of time, a velocity, an average velocity, or a peak velocity acquired from the ROI of a patient. When acquiring a patient parameter from a ROI, it is important for the ultrasound clinician to know that the acquisition quality was acceptable during the acquisition of the ultrasound data.

If the acquisition quality is not high enough, it is important that the clinician reacquires the ultrasound data before relying on any patient parameters calculated from the ultrasound data. However, with conventional ultrasound systems it is often difficult for the clinician to determine if the acquisition quality of the ultrasound data acquisition is acceptable. For these and other reasons an improved ultrasound imaging system and method is required that provides the clinician with feedback regarding the acquisition quality level that is intuitive to interpret and does not distract the clinician from viewing the ultrasound image displayed on the screen.

BRIEF DESCRIPTION OF THE INVENTION

The above-mentioned shortcomings, disadvantages and problems are addressed herein which will be understood by reading and understanding the following specification.

In an embodiment, a method of ultrasound imaging includes acquiring ultrasound data and acquiring a quality parameter during the process of acquiring the ultrasound data. The method includes determining, with a processor, an acquisition quality level based on the quality parameter. The method includes automatically selecting a first color based on the acquisition quality level from a group including at least the first color representing a first range of acquisition quality levels and a second color representing a second range of acquisition quality levels, where the second color is different than the first color and the second range of acquisition quality levels does not overlap with the first range of acquisition quality levels. The method includes generating an image based on the ultrasound data, displaying the image on a display device and displaying a border in the first color on the first image, where the border indicates a position of the ROI and the first color represents the acquisition quality level.

In an embodiment, an ultrasound imaging system includes a probe, a display device, and a processor in electronic communication with the probe and the display device. The processor is configured to control the probe to acquire ultrasound data, acquire a quality parameter during the process of acquiring the ultrasound data, determine an acquisition quality level based on the quality parameter. The processor is configured to select a first color based on the acquisition quality level from a group including at least the first color representing a first range of acquisition quality levels and a second color, that is different than the first color, representing a second range of acquisition quality levels, where the second range of acquisition quality levels does not overlap with the first range of acquisition quality levels. The processor is configured to generate an image based on the ultrasound data, display the image on the display device, display a border in the first color on the image, where the border indicates the ROI and the first color represents the acquisition quality level.

In an embodiment, a non-transitory computer readable medium having stored thereon, a computer program having at least one code section, said at least one code section being executable by a machine for causing said machine to perform one or more steps including acquiring ultrasound data and acquiring a quality parameter during the process of acquiring the ultrasound data. The steps including determining, with a processor, an acquisition quality level based on the quality parameter. The steps including automatically selecting a first color based on the acquisition quality level from a group including at least the first color representing a first range of acquisition quality levels and a second color representing a second range of acquisition quality levels, where the second color is different than the first color and the second range of acquisition quality levels does not overlap with the first range of acquisition quality levels. The steps including generating an image based on the ultrasound data, displaying the image on a display device, displaying a border in the first color on the first image, where the border indicates a position of the ROI and the first color represents the acquisition quality level.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
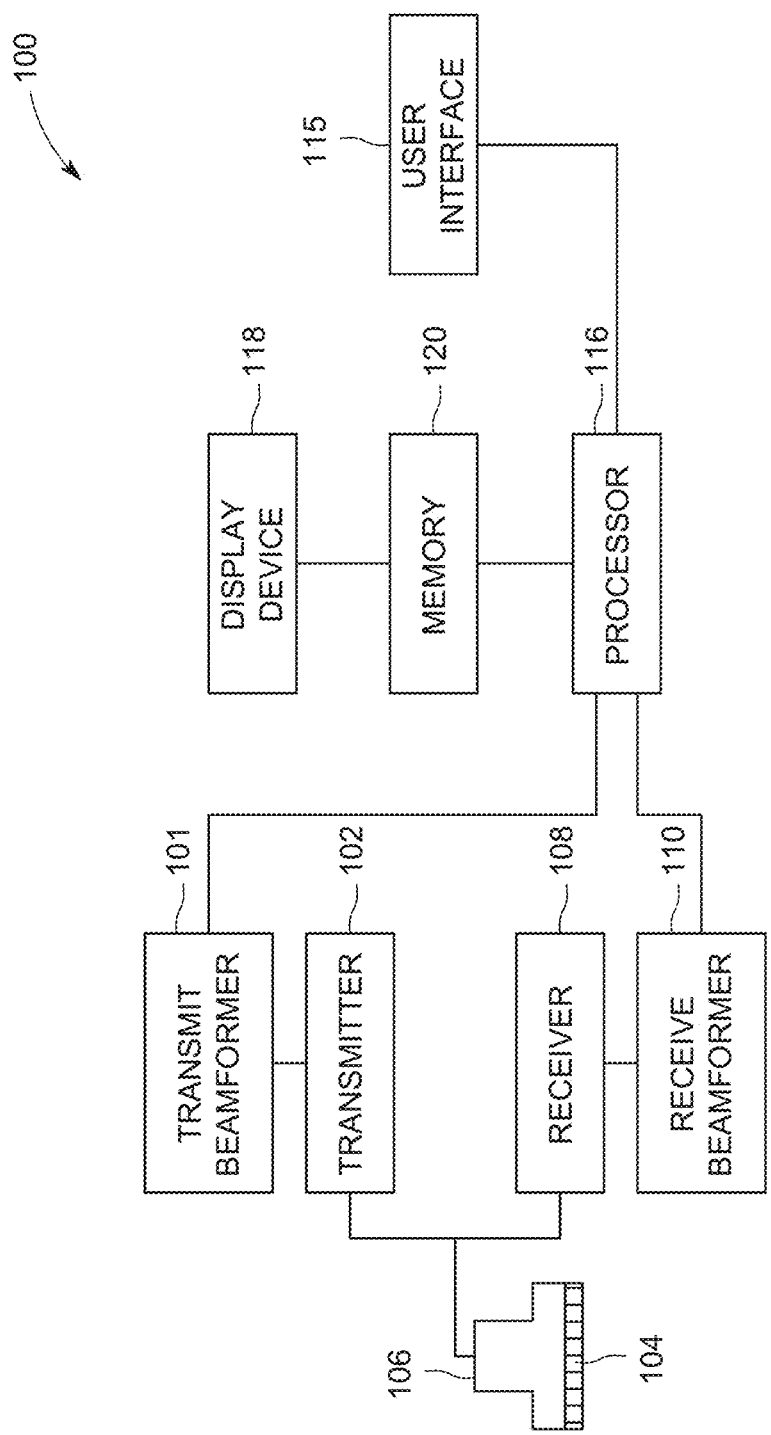
FIG. 1 is a schematic diagram of an ultrasound imaging system in accordance with an embodiment.

FIG. 1 is a schematic diagram of an ultrasound imaging system 100 in accordance with an embodiment. The ultrasound imaging system 100 includes a transmit beamformer 101 and a transmitter 102 that drive elements 104 within a probe 106 to emit pulsed ultrasonic signals into a body (not shown). The probe 106 may be any type of probe, including a linear probe, a curved array probe, a 1.25D array, a 1.5D array, a 1.75D array, or 2D array probe according to various embodiments. The probe 106 may also be a mechanical probe, such as a mechanical 4D probe or a hybrid probe according to other embodiments. The probe 106 may be used to acquire 4D ultrasound data that contains information about how a volume changes over time. Each of the volumes may include a plurality of 2D images or slices. Still referring to FIG. 1, the pulsed ultrasonic signals are back-scattered from structures in the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. According to some embodiments, the probe 106 may contain electronic circuitry to do all or part of the transmit beamforming and/or the receive beamforming. For example, all or part of the transmit beamformer 101, the transmitter 102, the receiver 108 and the receive beamformer 110 may be situated within the probe 106. The terms "scan" or "scanning" may also be used in this disclosure to refer to acquiring data through the process of transmitting and receiving ultrasonic signals. The terms "data" and "ultrasound data" may be used in this disclosure to refer to either one or more datasets acquired with an ultrasound imaging system. A user interface 115 may be used to control operation of the ultrasound imaging system 100. The user interface may be used to control the input of patient data, or to select various modes, operations, and parameters, and the like. The user interface 115 may include a one or more user input devices such as a keyboard, hard keys, a touch pad, a touch screen, a track ball, rotary controls, sliders, soft keys, or any other user input devices.

The ultrasound imaging system 100 also includes a processor 116 to control the transmit beamformer 101, the transmitter 102, the receiver 108 and the receive beamformer 110. The receive beamformer 110 may be either a conventional hardware beamformer or a software beamformer according to various embodiments. If the receive beamformer 110 is a software beamformer, it may comprise one or more of the following components: a graphics processing unit (GPU), a microprocessor, a central processing unit (CPU), a digital signal processor (DSP), or any other type of processor capable of performing logical operations. The beamformer 110 may be configured to perform conventional beamforming techniques as well as techniques such as retrospective transmit beamforming (RTB).

The processor 116 is in electronic communication with the probe 106. The processor 116 may control the probe 106 to acquire ultrasound data. The processor 116 controls which of the elements 104 are active and the shape of a beam emitted from the probe 106. The processor 116 is also in electronic communication with a display device 118, and the processor 116 may process the ultrasound data into images for display on the display device 118. For purposes of this disclosure, the term "electronic communication" may be defined to include both wired and wireless connections. The processor 116 may include a central processing unit (CPU) according to an embodiment. According to other embodiments, the processor 116 may include other electronic components capable of carrying out processing functions, such as a digital signal processor, a field-programmable gate array (FPGA), a graphics processing unit (GPU) or any other type of processor. According to other embodiments, the processor 116 may include multiple electronic components capable of carrying out processing functions. For example, the processor 116 may include two or more electronic components selected from a list of electronic components including: a central processing unit (CPU), a digital signal processor (DSP), a field-programmable gate array (FPGA), and a graphics processing unit (GPU). According to another embodiment, the processor 116 may also include a complex demodulator (not shown) that demodulates the RF data and generates raw data. In another embodiment the demodulation can be carried out earlier in the processing chain. The processor 116 may be adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. Real-time frame or volume rates may vary based on the size of the region or volume from which data is acquired and the specific parameters used during the acquisition. The data may be stored temporarily in a buffer (not shown) during a scanning session and processed in less than real-time in a live or off-line operation. Some embodiments of the invention may include multiple processors (not shown) to handle the processing tasks. For example, a first processor may be utilized to demodulate and decimate the RF signal while a second processor may be used to further process the data prior to display as an image. It should be appreciated that other embodiments may use a different arrangement of processors. For embodiments where the receive beamformer 110 is a software beamformer, the processing functions attributed to the processor 116 and the software beamformer hereinabove may be performed by a single processor such as the receive beamformer 110 or the processor 116. Or, the processing functions attributed to the processor 116 and the software beamformer may be allocated in a different manner between any number of separate processing components.

According to an embodiment, the ultrasound imaging system 100 may continuously acquire ultrasound data at a frame-rate of, for example, 10 Hz to 30 Hz. Images generated from the data may be refreshed at a similar frame-rate. Other embodiments may acquire and display data at different rates. For example, some embodiments may acquire ultrasound data at a frame rate of less than 10 Hz or greater than 30 Hz depending on the size of the volume and the intended application. For example, many applications involve acquiring ultrasound data at a frame rate of 50 Hz. A memory 120 is included for storing processed frames of acquired data. In an exemplary embodiment, the memory 120 is of sufficient capacity to store frames of ultrasound data acquired over a period of time at least several seconds in length. The frames of data are stored in a manner to facilitate retrieval thereof according to its order or time of acquisition. The memory 120 may comprise any known data storage medium.

Optionally, embodiments of the present invention may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 116 (e.g., B-mode, Color Doppler, M-mode, Color M-mode, spectral Doppler, Elastography, TVI, strain, strain rate, and the like) to form 2D or 3D images or data. For example, one or more modules may generate B-mode, color Doppler, M-mode, color M-mode, spectral Doppler, Elastography, TVI, strain, strain rate and combinations thereof, and the like. The image beams and/or frames are stored and timing information indicating a time at which the data was acquired in memory may be recorded. The modules may include, for example, a scan conversion module to perform scan conversion operations to convert the image frames from coordinates beam space to display space coordinates. A video processor module may be provided that reads the image frames from a memory and displays the image frames in real time while a procedure is being carried out on a patient. A video processor module may store the image frames in an image memory, from which the images are read and displayed. The ultrasound imaging system 100 may be a console-based system, a laptop, a handheld or hand-carried system, or any other configuration.

Figure 2:
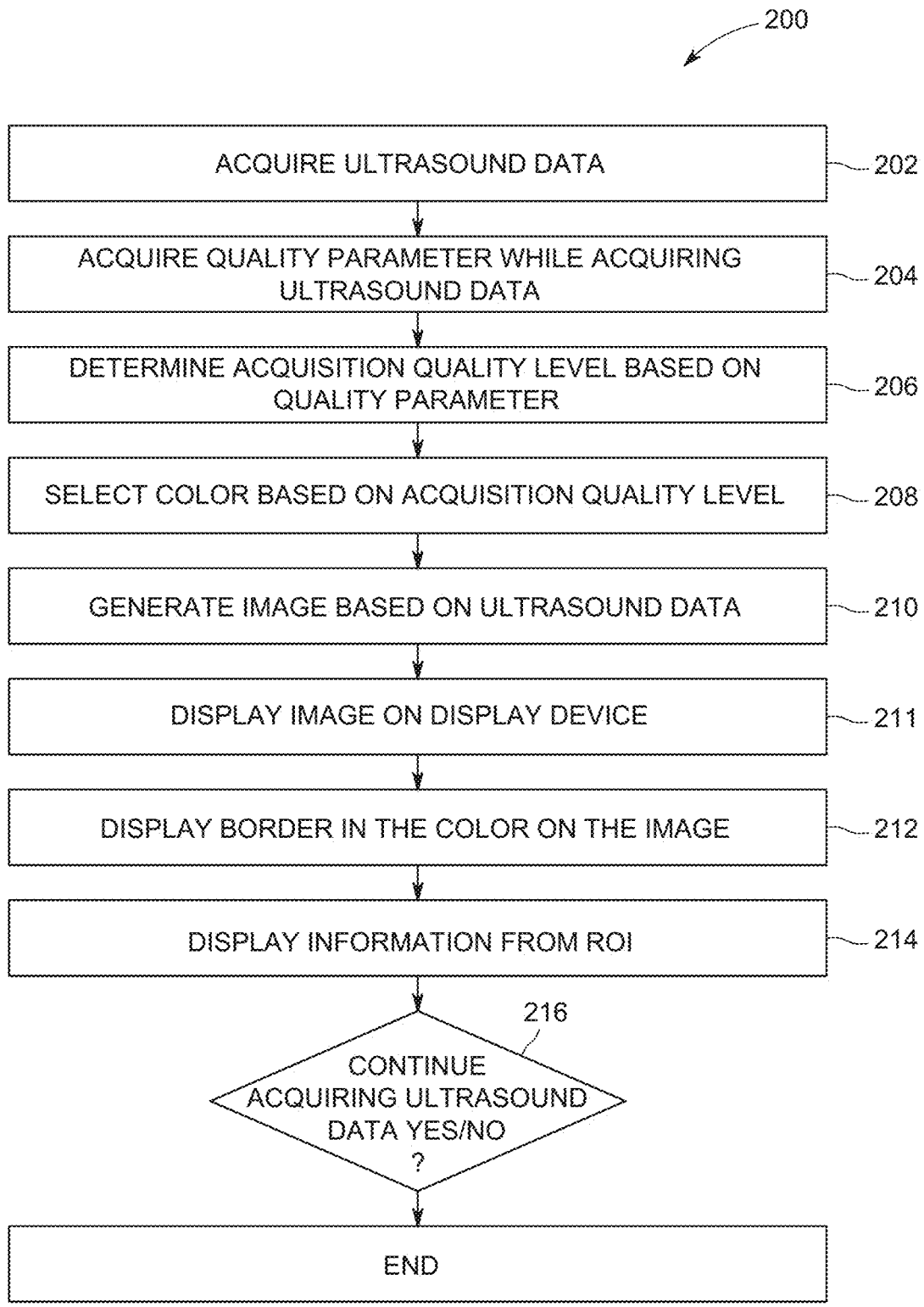
FIG. 2 is a flow chart in accordance with an embodiment.

FIG. 2 is a flow chart of a method 200 in accordance with an exemplary embodiment. The individual blocks of the flow chart represent steps that may be performed in accordance with the method 200. Additional embodiments may perform the steps shown in a different sequence and/or additional embodiments may include additional steps not shown in FIG. 2. The technical effect of the method 200 is the display of an image generated from ultrasound data and the display of a border indicating a position of an ROI in the image, where a color of the border represents the acquisition quality level.

FIG. 2 will be described in accordance with an exemplary embodiment where the method 200 is performed by the system 100 shown in FIG. 1. At step 202, the processor 116 controls the probe 106 to acquire ultrasound data from a region of a patient. The ultrasound data may include 1D ultrasound data, 2D ultrasound data, 3D ultrasound data or 4D ultrasound data. The ultrasound data may be acquired and displayed in real-time as part of a "live" ultrasound imaging procedure. Or, according to other embodiments, the ultrasound data may be acquired during a first discrete period of time, processed, and then displayed after processing.

At step 204, the processor 116 acquires a quality parameter during the process of acquiring the ultrasound data. The quality parameter may be any parameter that is correlated with the quality of the acquisition. Acquiring the quality parameter may include calculating the quality parameter from the ultrasound data according to some embodiments, while in other embodiments, acquiring the quality parameter may include acquiring a quality parameter based on data that is not ultrasound data. For example, the quality parameter may be acquired with a non-ultrasound sensor. The quality parameter may, for instance, include a noise level of the image, an amount of probe motion, a frame-consistency-over-time metric, a signal intensity, a correctness-of-view metric, a correctness of a flow spectral waveform, or any other parameter associated with acquisition quality. In general, a lower noise level is correlated with higher acquisition quality, a lower amount of probe motion is correlated with higher acquisition quality, and a higher frame-consistency-over-time is correlated with higher acquisition quality. The correctness-of-view metric may be calculated by comparing acquired image frames with a standard view using image correlation techniques. Some embodiments may employ deep learning and/or neural networks to determine how closely an acquired image frame matches a standard view.

At step 206, the processor 116 determines the acquisition quality level based on the quality parameter acquired at step 204. According to some embodiments, the processor 116 may determine the acquisition quality level based on 2 or more different quality parameters. Or, according to other embodiments, the processor 116 may determine the acquisition quality level based on only a single quality parameter.

Next, at step 208, the processor 116 selects a color based on the acquisition quality level. The processor 116 may select from at least a first color and a second color, where the second color is different than the first color. According to an embodiment, the first color may represent a first acquisition quality levels and the second color may represent a second acquisition quality. According to an embodiment, the first color may represent a first range of acquisition quality levels and that second color may represent a second range of acquisition quality levels, where the second range does not overlap with the first range. The first color may be, for example, green, and the first ranges of acquisition quality levels may represent acquisition quality levels that are considered acceptable. The second color may be, for example, red, and the second range of acquisition quality levels may represent acquisition quality levels that are unacceptable. The acquisition quality levels may be expressed on a numeric scale, such as, for example 1-10.

According to other embodiments, the processor 116 may select from more than two colors representing more than two discrete ranges of acquisition quality levels. For example, a first color, such as green, may represent a first acquisition quality level; a second color, such as yellow, may represent a second acquisition quality level; and a third color, such as red, may represent a third acquisition quality level. Or, the first color may represent a first range of acquisition quality levels, the second color may represent a second range of acquisition quality levels, and the third color may represent a third range of acquisition quality levels. The first range of acquisition quality levels, the second range of acquisition quality levels, and the third range of acquisition quality levels may each be discrete, non-overlapping ranges according to an embodiment. According to other embodiments, more than three different colors may be used to represent various acquisition quality levels or various ranges of acquisition quality levels.

According to an embodiment using three colors, green may be the first color and it may be used to represent an acquisition quality level that is high, red may be the second color and it may be used to represent an acquisition quality level that is low, and yellow may be the third color and it may be used to represent an acquisition quality level that is medium (i.e., in between the high acquisition quality level and the low acquisition quality level). The acquisition quality levels (i.e., high, medium and low, according to an embodiment) may be preset on the processor 116 at the factory or they may be user-definable. The user may, for instance, assign a range of quality parameter values to each acquisition quality level. Likewise, the user may assign various acquisition quality levels to acquisition quality values or the user may define a range of acquisition quality levels associated with each color.

Next, at step 210, the processor 116 generates an image based on the ultrasound data. The image may be a 1D image, a 2D image, a 3D image or a 4D image. The image may be generated from any mode of ultrasound data. For example, the image may be a B-mode image, a Color Doppler image, a M-mode image, a Color M-mode image, a spectral Doppler image, an Elastography image, a TVI image, or any other type of image generated from ultrasound data. The ultrasound data may be acquired and the image may be displayed in real-time as part of a "live" ultrasound imaging procedure. According to embodiments, the image may be a still frame generated from the ultrasound data. According to other embodiments, the processor 116 may generate images from two or more different imaging modes at step 210 based on the ultrasound data. For example, in a VTI mode, the processor 116 may generate both a B-mode image and a spectral Doppler image based on the ultrasound data. In an IVC mode, the processor 116 may generate both a B-mode image and an M-mode image based on the ultrasound data. At step 211, the processor 116 displays the image on the display device 118.

At step 212, the processor 116 displays a border in a color on the ultrasound image. The border indicates the position of an ROI within the image and the color represents the acquisition quality level. For example, according to the embodiment described above where the processor 116 selects from three different colors for the border, the border may be green if the acquisition quality level is high, the border may be yellow if the acquisition quality level is medium, and the border may be red is the acquisition quality level is low. The ROI may, for instance, indicate a region from which a specific parameter or data has been acquired or will be acquired.

At step 214, the processor 116 display information acquired from a portion of the patient corresponding to the ROI. Examples of types of information that may be displayed will be described hereinafter with respect to FIGS. 3-9.

At step 216, the processor 116 determines if it is desired to continue acquiring ultrasound data. If it is desired to continue acquiring ultrasound data, the method 200 may repeat steps 202, 204, 206, 208, 210, 211, 212, and 214. According to an embodiment where the ultrasound image is a live image, the steps 202, 204, 206, 208, 210, 211, 212, 214 and 216 may be iterated many times during the acquisition and display of the live image. The steps 204, 206, 208, 210, 211, 212, 214, and 216 may, for instance, all be performed multiple times during the process of acquiring the ultrasound data at step 202.

The method 200 will be described according to a specific embodiment with respect to FIG. 3. According to the embodiment shown in FIG. 3, the method 200 may be used to acquire pulse wave Doppler ultrasound data during a technique to calculate a velocity-time integral. The velocity-time integral may be calculated automatically or semi-automatically according to various embodiments.

Figure 3:
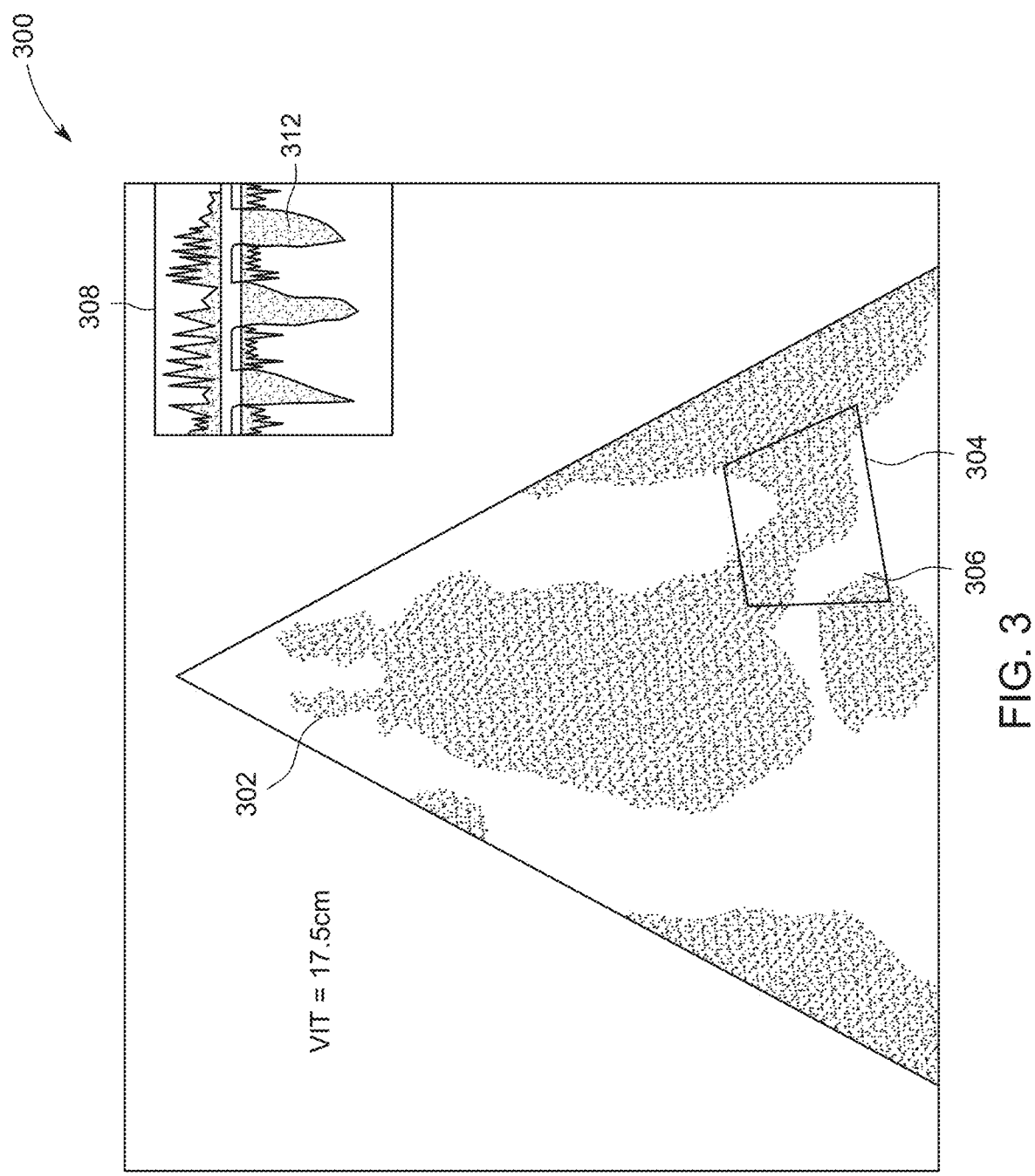
FIG. 3 is a schematic representation of an image in accordance with an embodiment.

Referring to FIGS. 2 and 3, at step 202 the processor 116 acquires both B-mode ultrasound data and pulse wave Doppler ultrasound data. At step 204, the processor 116 acquires a quality parameter during the process of acquiring the ultrasound data. According to an embodiment, the quality parameter may be acquired only during the process of acquiring the pulse wave Doppler ultrasound data. At step 206, the processor 116 determine the acquisition quality level and selects a color based on the acquisition quality level in a manner similar to that discussed above.

At step 210, the processor generates an image 302 based on the ultrasound data. The image 302 is a B-mode image generated from B-mode ultrasound data according to an embodiment. At step 212, the processor 116 displays a border 304 on the image to indicate the position of the ROI 306. The border 304 is the color that was selected at step 208 to represent the acquisition quality level during the process of acquiring the ultrasound data at step 202. According to an automated embodiment, the ROI 306 may be automatically positioned by the processor 116 based on pulse wave Doppler data and/or image data from the B-mode image 302. The processor 116 may determine the ROI 306 placement by identifying the ROI placement on the image 302 that yields pulse wave Doppler values that are consistent with the structure being analyzed. According to an embodiment, the processor 116 may position the ROI 306 on a portion of the image representing the left ventricle outflow tract. According to other embodiments, the ROI may be manually positioned on the B-mode image 302. At step 211, the processor 116 displays the image 302 on the display device 118.

FIG. 3 includes a pulse wave Doppler waveform 308 generated from pulse wave Doppler ultrasound data. Next, at step 214, the processor 116 displays information acquired from the ROI 306. According to an embodiment, the information may be a velocity time integral (VTI) value 310 calculated from the pulse wave Doppler image. The VTI value 310 represents an area 312 under the curve in the pulse wave Doppler image 308. The VTI value 310 is 17.5 cm according to the exemplary embodiment shown in FIG. 3.

The method 200 may iteratively repeat steps 202, 204, 206, 208, 210, 211, 212, 214 and 216. The B-mode image 302 and the pulse wave Doppler image 308 may be live ultrasound images that are updated as additional ultrasound data is acquired. The processor 116 may adjust the color of the border 304 to represent the acquisition quality level of the most recently acquired ultrasound data. The border 304 shown in FIG. 3 is a solid line around the ROI 306. According to other embodiments, the acquisition quality level may be determined for a fixed number of frames or a fixed period of time. For example, the processor 16 may calculate the acquisition quality level for the most recently acquired 30 frames, or any other number of frames. Likewise, the processor 116 may calculate the acquisition quality level for the ultrasound data acquired within the past 10 seconds, or any other amount of time. The processor 116 may update the color of the border 304 to represent a change in the acquisition quality level of the ultrasound data.

Displaying the border 304 in a color representing the acquisition quality level provides an easy and convenient way for the operator to determine the reliability of the information calculated from the ROI 306. The border 304 is unobtrusive and does not block structures within the B-mode image 302. The color of the border 304 may be updated in real-time as additional ultrasound data is being acquired, which provides the clinician with real-time feedback about the data quality while performing the procedure. Additionally, the border 304 is positioned around the ROI 306, which is where the clinician is most likely to be focusing his or her attention. As such, the clinician does not need to remove his/her gaze from the ROI 306 in order to determine the relative quality level of the acquisition quality level.

FIGS. 4, 5, 6, and 7 are schematic representations of various embodiments. FIGS. 4, 5, 6, and 7 show embodiments where the velocity time interval is automatically determined. Common reference numbers are used to identify identical elements in FIGS. 3, 4, 5, 6, and 7. Previously described elements will not be described again with respect to FIGS. 4, 5, 6, and 7.

Figure 4:
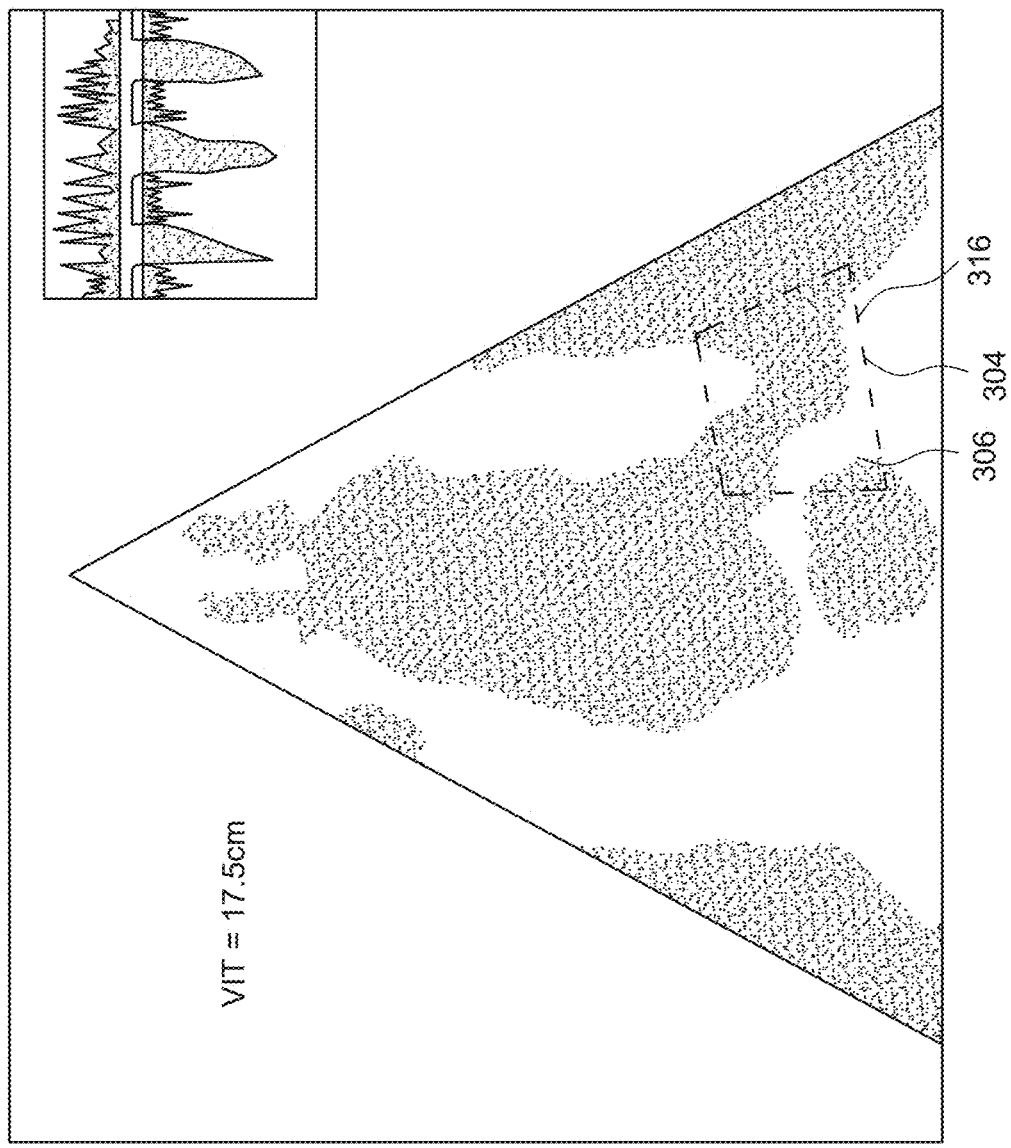
FIG. 4 is a schematic representation of an image in accordance with an embodiment.

FIG. 4 is a schematic representation of an embodiment where the border 304 of the ROI 306 is a dashed line 316.

Figure 5:
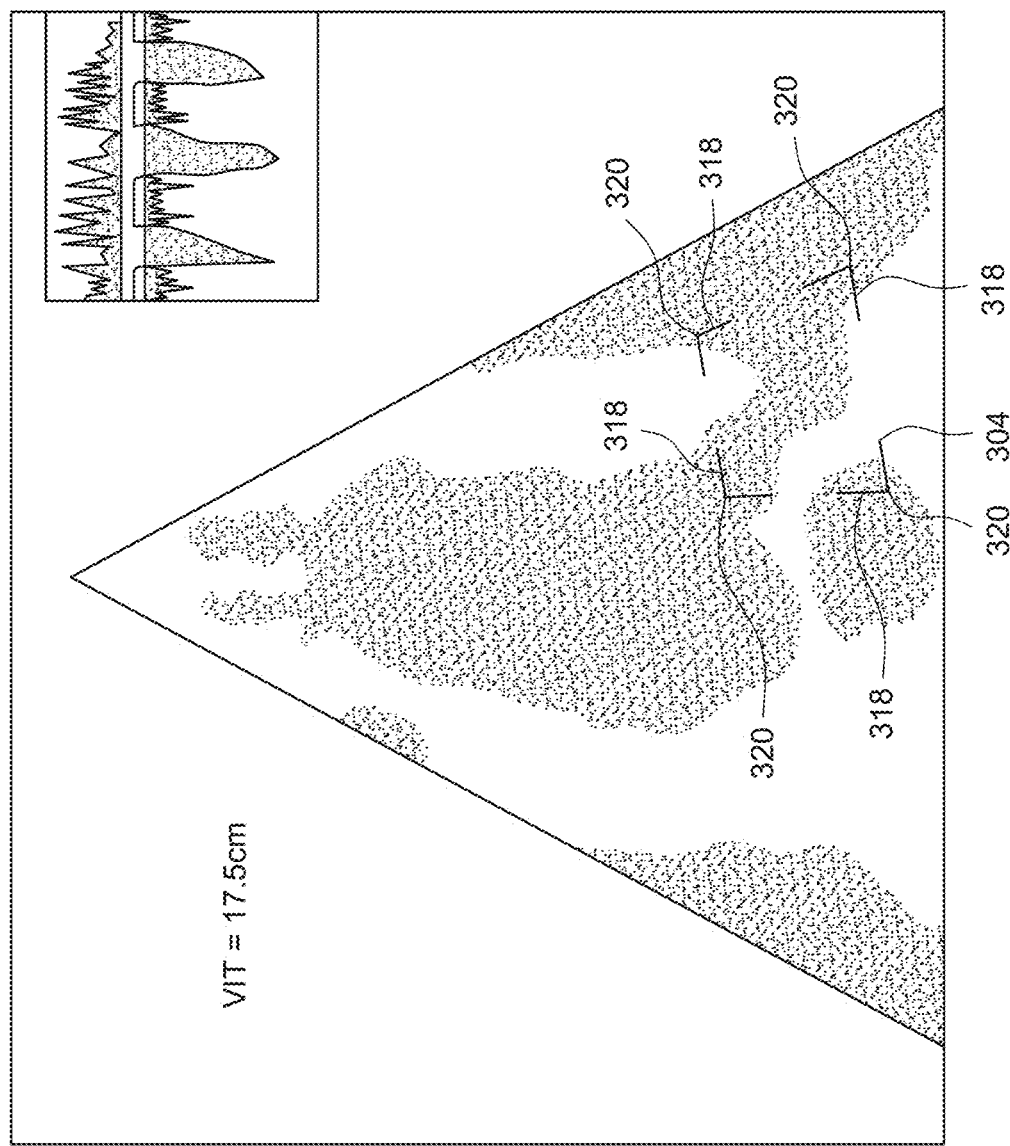
FIG. 5 is a schematic representation of an image in accordance with an embodiment.

FIG. 5 is a schematic representation of an embodiment where the border 304 of the ROI 306 comprises a plurality of corner markers 318. Each of the plurality of corner markers 318 comprises a pair of line segments disposed at an angle to each other. A point of intersection 320 is used to indicate the position of a corner of the ROI 306.

Figure 6:
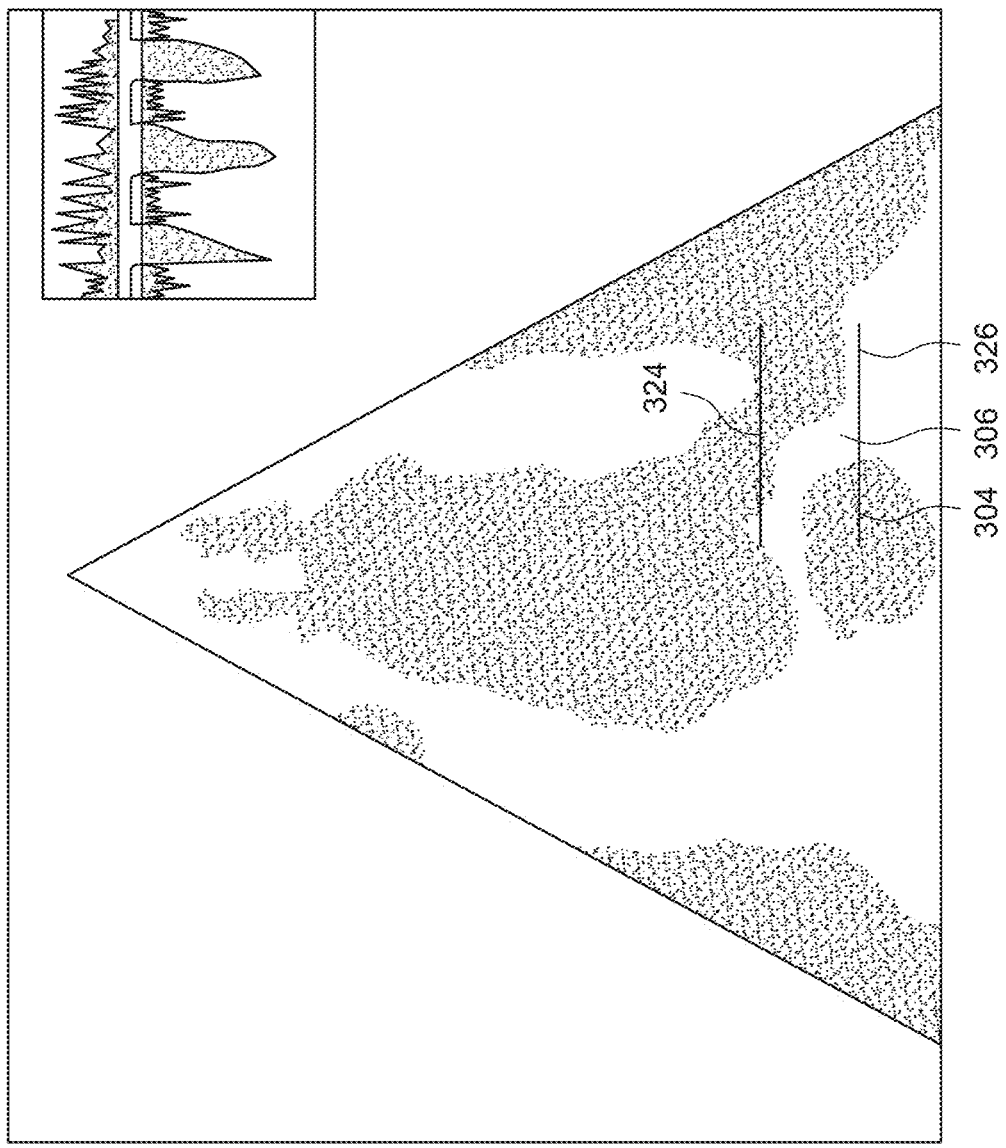
FIG. 6 is a schematic representation of an image in accordance with an embodiment.

FIG. 6 is a schematic representation of an embodiment where the ROI 306 is a rectangle and the border 304 includes a first horizontal line 324 and a second horizontal line 326. The first horizontal line 324 defines an upper border of the ROI 306 and the second horizontal line 326 defines a lower border of the ROI 306. The lengths of the first horizontal line and the second horizontal line 326 define the horizontal extent of the ROI 306.

Figure 7:
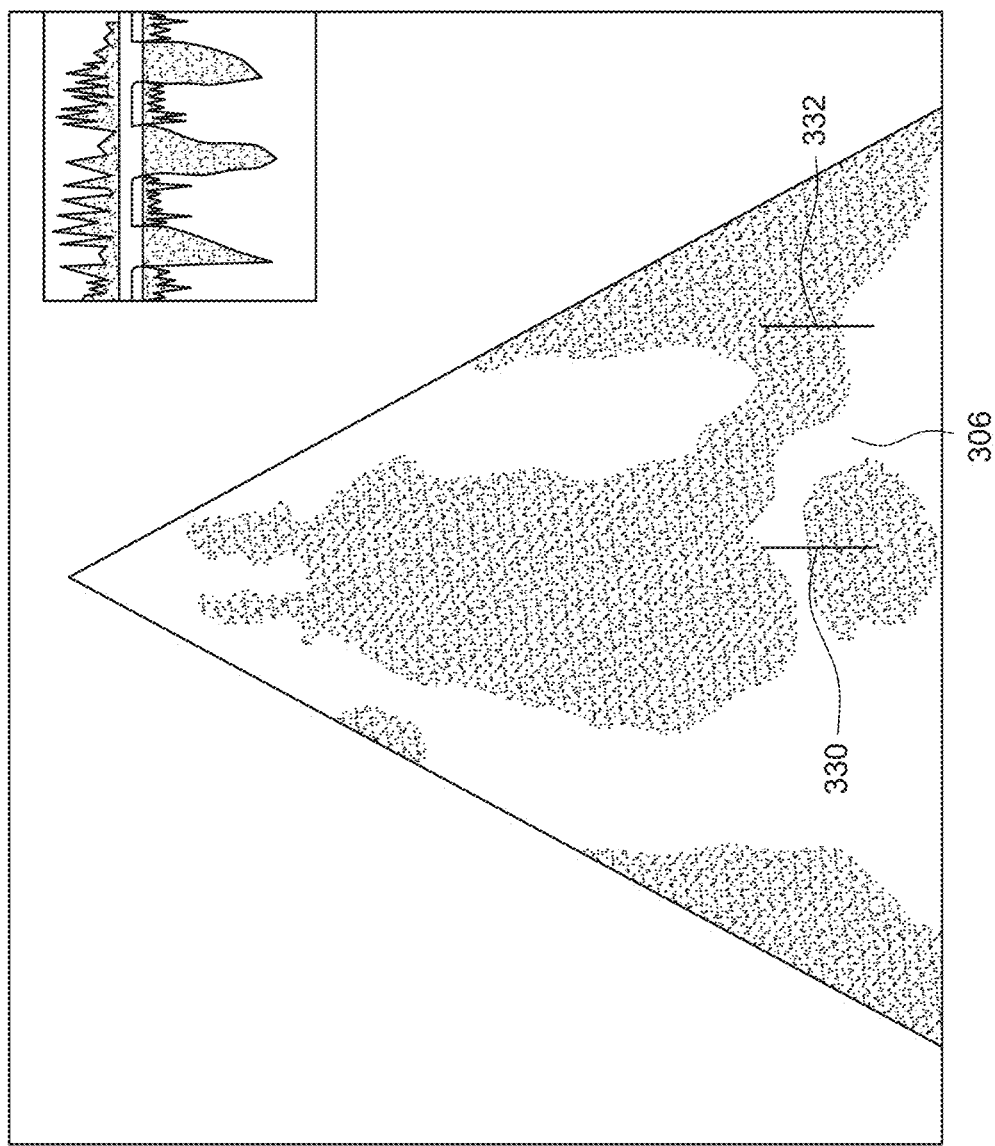
FIG. 7 is a schematic representation of an image in accordance with an embodiment.

FIG. 7 is a schematic representation of an embodiment where the border 304 of the ROI is a first vertical line 330 and a second vertical line 332. The lengths of the first vertical line 330 and the second vertical line 332 determine the vertical height of the ROI 306 and the horizontal distance between the first vertical line 330 and the second vertical line 332 determines the horizontal length of the ROI 306.

For modes that display images with time along an axis, such as M-mode or Spectral Doppler, one of the dimensions of the ROI may include time.

According to a second exemplary embodiment, the method 200 may be used to automatically count B-lines in an image. The method 200 will be described in according with an embodiment with respect to FIG. 8.

Figure 8:
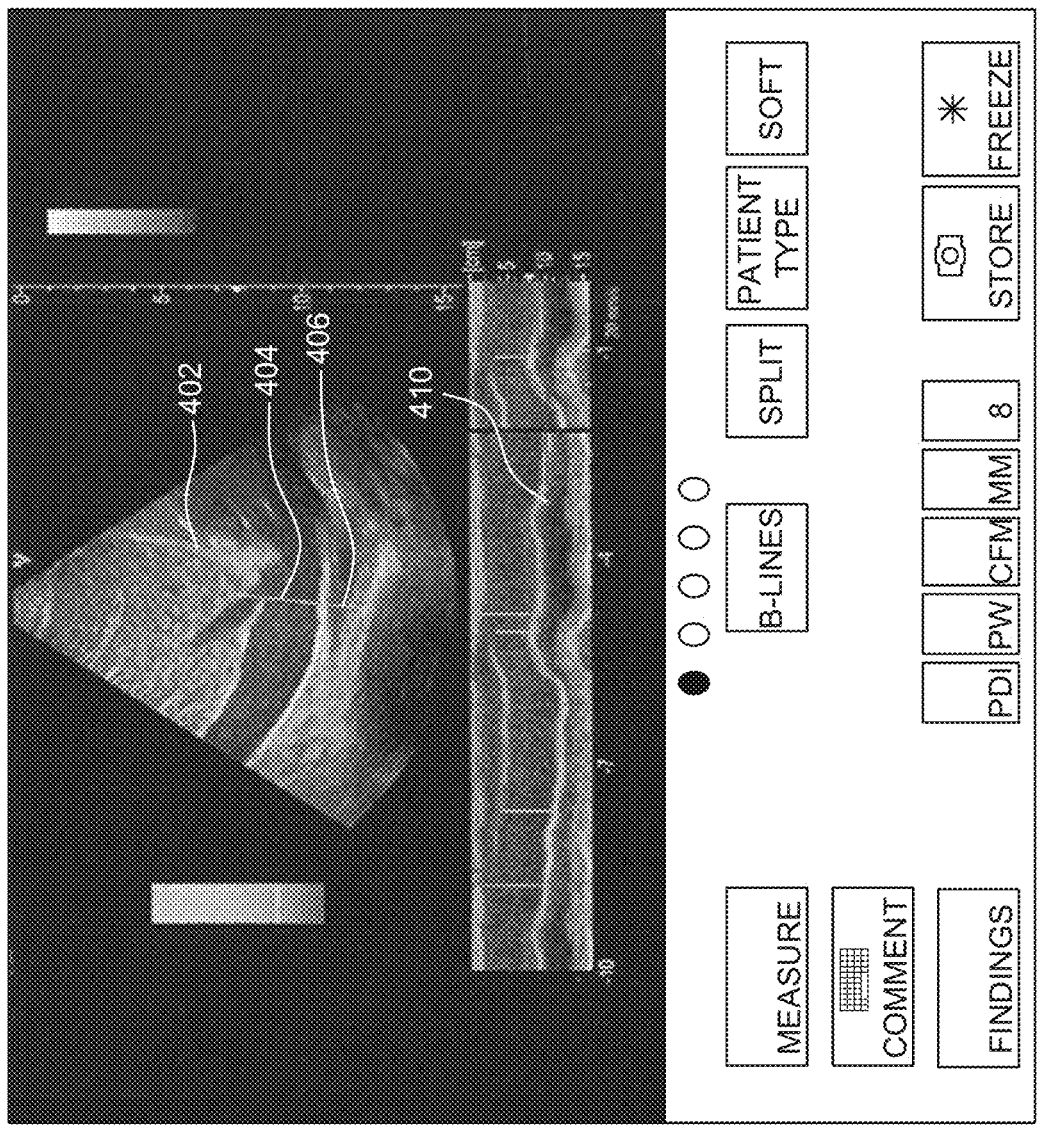
FIG. 8 is a schematic representation of an image in accordance with an embodiment.

Referring to both FIGS. 2 and 8, at step 202 B-mode ultrasound data is acquired. At step 204, one or more quality parameters are acquired during the process of acquiring the B-mode ultrasound data. The quality parameter may be a noise level of the image, an amount of probe motion, a frame-consistency-over-time metric, a signal intensity, a correctness-of-view metric, or any other parameter associated with acquisition quality. At step 206, the processor 116 determines an acquisition quality level based on the one or more quality parameters acquired at step 206 in a manner similar to that described hereinabove. According to an exemplary embodiment, the quality parameter may be the amount of probe motion and the processor may determine the acquisition quality level based on the amount of probe motion during the acquisition of the B-mode ultrasound data. Next, at step 208, the processor 116 selects a color based on the acquisition quality level. As described hereinabove, the processor 116 may select green for a high acquisition quality level and red for a low acquisition quality level.

At step 210, the processor 116 generates an image 402 based on the B-mode ultrasound. The image 402 may be a live image that updates in real-time as additional ultrasound data is acquired according to an embodiment. At step 212, the processor displays a border 404 on the image. The border 404 is a line 406 according to an exemplary embodiment. The line 406 indicates the ROI, which is a two-dimensional ROI. According to the embodiment shown in FIG. 8, M-mode ultrasound data is acquired along the line 406. The acquisition of M-mode data may be interleaved with the acquisition of B-mode ultrasound data while the ultrasound data is acquired at step 202. The line 406 is shown in the color that was selected at step 208. At step 211, the processor 116 displays the image 402 on the display device 118.

At step 214, information from the ROI indicated by the line 406 is displayed on the display device 118. The information is an M-mode trace 410 according to the embodiment shown in FIG. 8. At step 216, the processor 116 determines if it is desired to continue acquiring ultrasound data. If it is desired, the method 200 returns to step 202, where steps 202, 204, 206, 208, 210, 211, 212, 214, and 216 are repeated. Steps 202, 204, 206, 208, 210, 211, 212, 214, and 216 may be repeated many times during the display of a live ultrasound image. According to an embodiment, the processor 116 may alter the color of the line 404 in response to a change in the acquisition quality level as determined based on the quality parameter acquired at step 204. The color of the line 406 indicating the ROI may therefore inform the clinician about the acquisition quality level of the ultrasound data acquired at step 202 in real-time.

Figure 9:
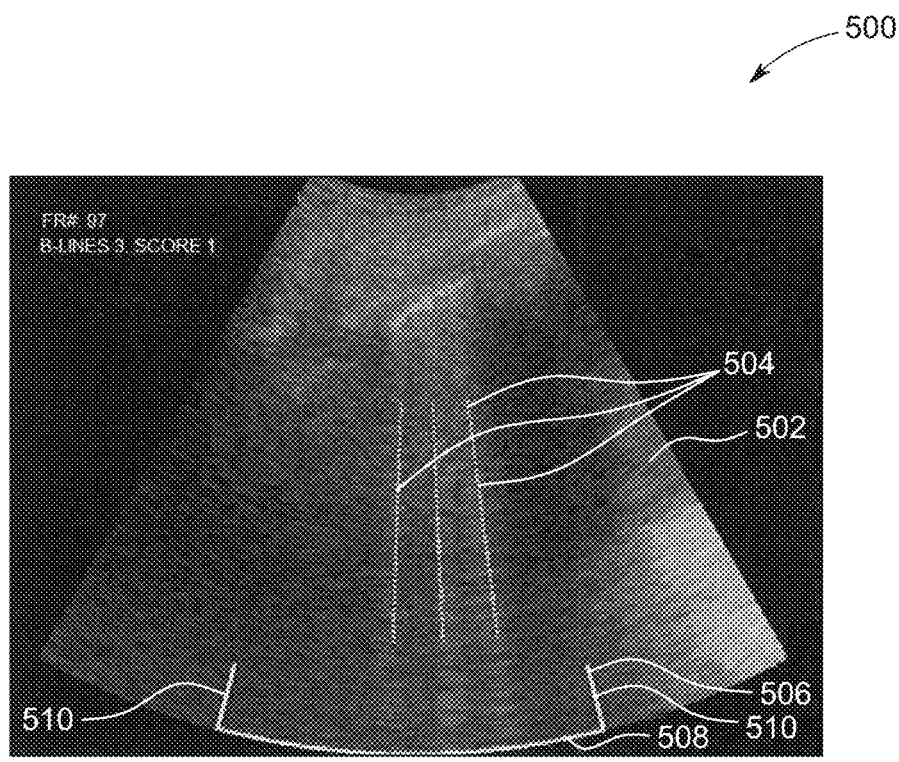
FIG. 9 is a schematic representation of an image in accordance with an embodiment.

FIG. 9 is a schematic representation of a display 500 generated according to an embodiment. The display 500 includes a B-mode image 502. The B-mode image 502 includes a plurality of B lines 504. A border 506 is shown to indicate the ROI from which the processor 116 calculates the number of B lines 504 present in the image 502. According to an embodiment, the processor 116 may automatically select the frame showing the image 502 by selecting the image 502 from a plurality of frames acquired over a period of time. The border 506 comprises an arc 508 and a pair of end brackets 510. The arc 508 and end brackets 510 may be positioned to indicate a sub-region of an imaging sector. The border 506 is shown on the image 502 in a color to represent the acquisition quality level in a manner similar to that described hereinabove with respect to other embodiments.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A method of ultrasound imaging comprising:
   continuously acquiring frames of ultrasound data with a probe at a frame rate of at least 10 Hz;
   generating live images in real-time based on the continuously acquired frames of ultrasound data;

displaying the live images of the acquired frames in real-time on a display device;
employing a neural network to calculate a quality parameter for the live images; and
displaying a color-coded line to visually represent the quality parameter on the display device, wherein the color-coded line is continuously updated in real-time to represent the quality parameter, and wherein the color-coded line represents a border of the live images.

2. The method of claim 1, wherein the quality parameter includes at least a correctness-of-view metric.

3. The method of claim 2, wherein the correctness-of-view metric is based on a determination of how well the live images match a standard view.

4. The method of claim 3, wherein the correctness of view metric is determined by applying a neural network to determine how closely the acquired image frames match a standard view.

5. The method of claim 1, wherein the color-coded line is generated using at least a first color and a second color that is different than the first color.

6. The method of claim 5, wherein the first color is green and the second color is yellow.

7. The method of claim 5, wherein the color-coded line is further generated using a third color that is different than both the first color and the second color.

8. The method of claim 1, wherein the color-coded line is displayed below at least a portion of the displayed live images.

9. The method of claim 1, wherein the color-coded line is a dashed line.

10. The method of claim 1, wherein the color-coded line is displayed above at least a portion of the displayed live images.

11. An ultrasound imaging system comprising:
a probe;
a display device; and
a processor in electronic communication with the probe and the display device, wherein the processor is configured to:
control the probe to continuously acquire frames of ultrasound data at a frame rate of at least 10 Hz;
generate live images in real-time based on the continuously acquired frames of ultrasound data;
display the live images of the acquired frames in real-time on a display device;
employ a neural network to calculate a quality parameter for the live images; and
display a color-coded line to visually represent the quality parameter on the display device, wherein the color-coded line is continuously updated in real-time to represent the quality parameter, and wherein the color-coded line represents a border of the live images.

12. The ultrasound imaging system of claim 11, wherein the quality parameter includes at least a correctness-of-view metric.

13. The ultrasound imaging system of claim 12, wherein the correctness-of-view metric is based on a determination of how well the live images match a standard view.

14. The ultrasound imaging system of claim 13, wherein the correctness-of-view metric is determined by applying a neural network to determine how closely the acquired image frames match a standard view.

15. The ultrasound imaging system of claim 11, wherein the color-coded line comprises at least a first color and a second color that is different than the first color.

16. The ultrasound imaging system of claim 15, wherein the first color is green and the second color is yellow.

17. The ultrasound imaging system of claim 15, wherein the color-coded line further comprises a third color that is different from both the first color and the second color.

18. The ultrasound imaging system of claim 11, wherein the processor is configured to display the color-coded line below at least a portion of the displayed live images on the display device.

19. The ultrasound imaging system of claim 11, wherein the color-coded line is a dashed line.

20. The ultrasound imaging system of claim 11, wherein the processor is configured to display the color-coded line above at least a portion of the displayed live images on the display device.

* * * * *